United States Patent [19]

Correa et al.

[11] Patent Number: 5,312,386
[45] Date of Patent: May 17, 1994

[54] DISPOSABLE SANITARY PAD

[75] Inventors: Mauro F. C. Correa, Sao Paulo; Rosana R. D. Neves, Sao Jose Dos Campos, both of Brazil

[73] Assignee: Johnson & Johnson, New Brunswick, N.J.

[21] Appl. No.: 942,477

[22] Filed: Sep. 9, 1992

Related U.S. Application Data

[63] Continuation of Ser. No. 852,358, Mar. 17, 1992, abandoned, which is a continuation of Ser. No. 706,141, May 29, 1991, abandoned, which is a continuation of Ser. No. 477,288, Feb. 8, 1990, abandoned.

[30] Foreign Application Priority Data

Feb. 15, 1989 [BR] Brazil .................................. 8900666

[51] Int. Cl.$^5$ .............................................. A61F 13/15
[52] U.S. Cl. .................................... 604/379; 604/385.1
[58] Field of Search ................. 604/379, 383, 385.1, 604/378, 380

[56] References Cited

U.S. PATENT DOCUMENTS

| | | | |
|---|---|---|---|
| 2,705,498 | 4/1955 | Johnson | 604/379 |
| 3,327,708 | 6/1967 | Sokolowski | 604/379 |
| 3,575,174 | 4/1971 | Mogor | 128/290 |
| 4,059,114 | 11/1977 | Richards | 128/287 |
| 4,184,498 | 1/1980 | Franco | 604/375 |
| 4,655,759 | 4/1987 | Romans-Hess et al. | 604/385 R |
| 4,701,177 | 10/1987 | Ellis et al. | 604/379 |
| 4,752,349 | 6/1988 | Gebel | 604/385.1 |
| 4,758,240 | 7/1988 | Glassman | 604/379 |
| 4,773,905 | 9/1988 | Molee et al. | 604/378 |
| 4,886,697 | 12/1989 | Perdelwitz, Jr. et al. | 604/385.1 |
| 4,936,839 | 6/1990 | Molee et al. | 604/385.1 |
| 5,019,070 | 5/1991 | Ruben | 604/385.1 |

FOREIGN PATENT DOCUMENTS

0136524A1 10/1985 European Pat. Off. .
0249405A2 12/1987 European Pat. Off. .

Primary Examiner—Randall L. Green
Assistant Examiner—Mary Beth Jones

[57] ABSTRACT

This invention relates to a disposable sanitary napkin having longitudinal edges and transverse ends, having at least one compression line extending along and close to the longitudinal edges, such that the pressure of the user's thighs on the product will bring about a protuberance of absorbent material toward the perineal area when worn. The products of this invention thus bring the absorbent material closer to the point of discharge of menstrual fluid, which is the critical cause of leakage from the longitudinal edges of sanitary napkins.

19 Claims, 3 Drawing Sheets

DISPOSABLE SANITARY PAD

This patent application is a continuation of U.S. Ser. No. 852,358, filed Mar. 17, 1992 and now abandoned, which was a continuation of U.S. Ser. No. 706,141, filed May 29, 1991 and now abandoned, which was in turn a continuation of U.S. Ser. No. 477,288, filed Feb. 8, 1990 and now abandoned.

FIELD OF THE INVENTION

The present invention refers to disposable sanitary pads that Provide a lesser frequency of leakage.

More specifically, it refers to disposable sanitary pads that provide a more effective contact of the product with the external area of the perineal region of a user, thus reducing the risk of leakage from the sides of the product.

BACKGROUND OF THE INVENTION

In the scope of the invention, one considers hygienic pads those absorbing devices intended to be used outside the feminine body, usually during her menstrual periods, to receive and retain menstrual and other vaginal discharges.

Disposable sanitary pads are designed to be abandoned after they have collected the fluids from the feminine body, without being used once again.

Sanitary pads are items of general consumption in modern society and, for explanatory purposes, they can be divided into three categories, namely:
tampons
external pads
hybrid pads, which have characteristics of the other two types.

Tampons are pads that have the capacity of intercepting menstrual discharge within the vaginal duct with little risk of soiling the user's clothes. They are considered superior protection means. In practice failures can occur in their functioning as regards their capacity of effectively having radial expansion in function of the fluid that causes expansion of the pad, thus sealing and creating occlusion within the vaginal duct. Besides, there are people who, for physical or psychological reasons, are incapable of using tampons as effective feminine protection means. Finally, they can present insertion or removal problems; sometimes they are sticky and difficult to handle, and in certain health cases there is some medical restriction.

The so-called hybrid Pads are those that incorporate characteristics of tampons and external sanitary pads. Sometimes they are called wads or labial pads or vestibule-type Pads, in which case a Partial or total insertion into the vulvar vestibule occurs.

In many of the cases described in the literature, one does not take into account the anatomical cooperation with the user's body to the effect that the sensitive tissues are often distended by the obstructive geometry of certain structural elements, that is to say, the so-called labial pads find their functioning in friction contact with very sensitive urogenital parts such as the vaginal orifice, the urethral orifice and/or the clitoris. In other cases, it is stated that a pad should be firmly fastened to the user's intimate clothes with a portion of the pad located inside the vestibule, and under most circumstances this creates a friction effect inside that sensitive part.

Thus, according to U.S. Pat. Nos. 2,092,342 and 3,905,372, an element inside the vaginal opening is physically connected to an external part, so that the relative movement between the user's body and the underlying structure of the Pad causes discomfort, irritation and even pain. In a similar way, U.S. Pat. No. 3,983,873 describes flaps that are supported against the walls of the labial space, in order to increase the retaining forces of the pad. There are other vestibule-type Pads which are designed to eliminate this irritation factor by relative movement involving body/product/user's clothes, as in U.S. Pat. No. 4,742,245; however, the disclosed Product is extremely sophisticated and is expensive to manufacture.

External sanitary pads have been developed for use outside the body near the vulvar region, to collect the menstrual fluid, other vaginal discharges and possibly urine of incontinent women.

In their simplest and more traditional form, such Pads comprise an absorbent core placed between a fluid-permeable facing sheet (sometimes referred to as a "top sheet") and a fluid-impermeable backing sheet.

The absorbent core, sometimes referred to herein as the "absorbing element", is adapted to receive and absorb the menstrual discharge and other vaginal discharges. The absorbent core may comprise comminuted wood pulp fibers, Polymer foams, vegetable pulp, natural or synthetic fibers or any other material which can absorb menstrual fluids or the like body discharges. Wood pulp fibers are commonly used as the major constituent of the absorbent core of external sanitary pads.

The fluid-permeable facing sheet contacts the wearer's body when the sanitary pad is in use and permits the menstrual or other vaginal discharge to pass therethrough so as to be absorbed by the underlying absorbent core. This facing sheet usually comprises a fluid-permeable nonwoven fabric or a perforated plastic film. Although the facing sheet may be hydrophilic in nature, it is preferred that it be hydrophobic in nature. In the latter case, the menstrual or other discharge Passes through the fluid-permeable facing sheet but the sheet, owing to its hydrophobic nature, tends to remain dry to the touch, thus making the product more comfortable in use. Perforated Plastic films are usually inherently hydrophobic. Nonwoven fabrics, if they are not made of hydrophobic fibers, can be rendered hydrophobic by treatment with, e.g. a repellent finish such as that provided by fluorochemicals, wax emulsions or the like.

The purpose of the fluid-impermeable backing sheet, as its name suggests, is to prevent the fluid collected by the absorbent core from leaking from the sanitary pad and staining the clothing of the user. The backing sheet usually comprises a thin film of plastic such as polyethylene, although in some cases it might also comprise other materials, e.g. a nonwoven fabric, which has been suitably treated so as to be liquid impermeable. If desired, the backing sheet may be moisture vapor permeable, that is, it may allow moisture vapor to pass therethrough while at the same time preventing the passage of liquids.

Leakage, and the most most common is usually leakage of menstrual blood at the sides, even in very small amounts, is a great discomfort and embarrassment for the user. For those skilled in the art, the goal aimed at in developing such products is maximization of the flow of liquid in direction Z (taking into account that, in a graph for three-dimensional representation, axes X and Y represent the horizontal plane, and axis Z is perpendicular to them), since, in addition to the technical reasons that fully justify this objective, there are psychological reasons which show that a rapid Z-directional flow minimizes the stain effect on the pad and, associated with conditions of relatively dry top sheet, it has to do with the feeling of safety, thus reducing the possibility of embarrassment due to the failure of the pad, i.e. leakage.

The external pad of the traditional type is merely an elongated rectangular product, made without any worry about the user's anatomy. Thus, when in use, such a product may undergo deformation that detracts from its performance considerably and favors frequent leakage.

Starting therefrom the improvements have followed one another until the present prior art and have resulted, either directly or indirectly, in lesser possibility of leakage:

by forming the absorbing sheets more anatomical than a rectangle, for instance in the form of an hourglass;

by causing the pad as a whole to take on the form of a shell in order to fit between the user's legs in a better manner and be closer to her perineal area;

by using top sheets that optimize the passage of liquid towards the absorbing element and restrict the return thereof in the opposite direction;

by creating more elaborate structures, for instance, an absorbing element which is thicker in its central area to bring about more proximity between the point of discharge and the pad, side flaps that form barriers for leakage, overlapped structures such as in U.S. Pat. No. 4,425,130, and others;

by creating more absorbency by utilizing either absorbing fibers or superabsorbing polymers, by varying the density inside and along the traditional absorbing sheet or with layers of varied materials, and others.

From this list of improvements it can be seen that the optimization of the product with increasing complexity and sophistication tends to make the product more and more expensive with respect to the benefit obtained, which consequently raises the price for the final consumer.

An examination of the reasons for the existence of leakage in external sanitary pads indicates that it is necessary to minimize the course of the vaginal discharge to the Point at which it meets the Product that will collect and retain such liquids. This is justified by the fact that any course allows the fluid to flow over the skin adjacent the place of discharge, to a greater or lesser extent, obviously depending, for instance, upon the viscosity and the surface tension of such a liquid. In this way, in some cases it can even fall out of the reach of the absorbing sheet and leak, thus causing discomfort, embarrassment and the consequent feeling of unsafety for the user. The conclusion is that a structure with an excellent intrinsic performance as regards absorption and leakage retention can function only from the moment at which the contact of the liquid with such a structure occurs, not before.

SUMMARY OF THE INVENTION

Thus, knowing the shortcomings of the prior art and the functional needs after which those skilled in the art have been seeking in this kind of product, as per the foregoing considerations, one of the objects of the present invention is to provide an external disposable sanitary pad that will effectively minimize the risk of leakage at the sides.

Another object is to provide an effective Pad without employing new materials and without making use of complex and sophisticated structures that are difficult to manufacture.

Still another object of the present invention is to provide an effective and simple pad having a high cost/benefit ratio.

In accordance with the present invention there is provided a disposable sanitary pad characterized by containing at least one line obtained by compression along and near each longitudinal edge of the body of said pad. Such lines are sufficiently apart from each other, so that the pressure exerted by the user's thighs on said product in use will provide a protuberance towards the user's body, onto which liquids are discharged.

The functioning of the pad of the invention is based on the fact that, when put into use, the product is compressed on its central Part by the user's thighs. This compression causes the material contained between the two lines, to be forced toward the user's body, thus making a greater amount of material available for absorption close to the discharge point, where the need for absorption is more critical, in order to Prevent the liquid from having a free course with the possibility of escape over the skin, thus reducing the risk of leakage.

When the two lines are not present, as is the case of the prior art, the absorbing material under the pressure of the user's thighs tends to move away from her body, or still to take on a casual conformation that does not provide a better contact at the discharge point.

This means that, unlike what exists in the prior art, the disposable sanitary pad of the invention manages to provide a protuberance of absorbing material, to optimize the contact with the user's body, without the need for using additional absorbent material for this purpose.

As used herein, the expression "compression line" or "line obtained by compression" means that the body of the sanitary pad is subjected to a pressure along a line sufficient to create, in a non-resilient manner, a greater density with respect to the surrounding material. Such lines — there are at least two of them — may or may not be straight, parallel to each other and to the longitudinal edges, and can have any thickness. Preferably, the lines are parallel to the longitudinal edges and their width is less than 5 mm, since in this way they will favor the formation of the protuberance when the product is put into use.

Between a line created by a low compression, a Poorly defined one, and another created by a higher compression, a more defined one, the latter is preferred, since it intensifies the capacity of an absorbing sheet to form the protuberance toward the user's body under the Pressure of her thighs. However, a compression beyond a certain value has the disadvantage of creating a line of hard material to the extent of detracting from the user's comfort. The existence of a single compression line along each longitudinal edge is preferred. However, two or more lines close to each other along each longitudinal edge, or any other configuration that is not considerably detrimental to the appearance of the protuberance during use of the product are also included in the scope of the invention.

As used in this text, the expression "longitudinal edges" means the edges along the length of the absorbing material of the sanitary pad of the invention. This expression does not refer to the ends along the length of the product which can also have side flaps that extend beyond the absorbing element.

The expression "along and close to each longitudinal edge", as used here, means that the distance from one line obtained by compression to the nearest longitudinal edge is smaller than the distance between said one line and the other line obtained by compression near the opposite longitudinal edge. Since the compression lines are regions of preferential conduction of liquids due to their greater density, they are not so close to the longitudinal edges to the extent there is a risk of leakage, nor are they so close to each other that the formation of the aforementioned protuberance is hindered. Preferably, the distance from the compression line to the nearest longitudinal edge is of from about 5 to about 30% of the breadth of the absorbing element, and more preferably from about 5 to about 20% of the breadth of the absorbing element.

The distance between the compression lines is also a function of the material or materials that constitute the absorbing element, which vary in resilience, density, fiber length, etc. An intrinsic property of the compression lines known to those skilled in the art and that can be associated with the invention is that they provide a preferential way Of liquid conduction and serve to conduct (or "wick") the discharged fluid to regions further away from the point of discharge, that is to say, they serve to spread the liquid along the whole absorbing element in a more homogeneous and rapid manner, thus providing less time of contact of the liquid with the user's skin and helping to avoid leakage, which would happen in the event of an abundant menstrual discharge in a single place without compression lines to help to distribute it.

Some quite common practical embodiments of sanitary pads made use of elastic means associated with side flaps along the length of the product and of a batt of wood-pulp fibers as an absorbing element; it should be noted that a certain compactation of the absorbing element occurs during storage of the product. Such elastic means provide the product with anatomical curves and folds, and the resilience of the wood-pulp fibers causes the latter to settle in a Preferential manner near the anatomical curves and folds, thus giving way to undesired regions of higher density and, therefore, of lesser absorption speed, usually around the focus of menstrual discharge. The compression lines impart cohesion to the pulp panel, thus providing it with resistance to resilient movements of its fibers at places beneficial to the product, i.e. along the longitudinal edges, where they can lead the discharged liquid to more remote regions of the absorbing element and provide the aforementioned protuberance when in use.

As used herein, the term "body" of the pad is understood to comprise at least the absorbing element and can include any other layers, e.g. the facing sheet and the backing sheet, placed on, under or inside it. Thus, the compression lines may be impressed only upon the absorbing element, if so desired, or on any other structural element comprising the body of the pad. For example, the compression lines may be made in both the facing layer and the absorbing element.

The preferred method for creating the compression lines is by placing on the absorbing body a relief pattern made of an adequate material having the desired form and pressing it to mark the material of the absorbing element sufficiently to create the compression lines, by hot-pressing if necessary. The surface of the absorbing element put into contact with the relief pattern is the one facing the user's body; otherwise the pressure exerted by the user's thighs would undesirably favor the formation of the protuberance on that surface of the absorbing element facing away from the body.

An example of industrial realization consists in providing a rotatory cylinder with various equal relief patterns arranged along its perimeter and Passing the absorbing-element batts between this cylinder and a moving belt under pressure sufficient to provide the compression lines on said batts.

The disposable sanitary pad of the invention is not limited to any specific type of structure and can optionally comprise:

liquid-permeable cover sheets of nonwoven fabric or perforated plastic films, either with or without embossing, either separate or in combination with other materials, having either hydrophobic or hydrophilic characteristics, and others;

a unilayer or multilayer sheet made of wood pulp or other vegetable pulp, polymeric or natural foam, hydrophobic fibers, either separate or mixed among themselves, containing superabsorbing polymers with areas having differentiated densities, etc.;

either with or without means to attach it to the user's clothes;

an external backing sheet made of either totally or partially hydrophobic material or materials, whether respirable or not, monolayer or multilayer, etc.;

either with or without the presence of elastic means;

rectangular, in the form of an hourglass or any other adequate form.

The compression lines are necessarily located close to the longitudinal edges of the region designed to receive the menstrual discharge and should have a length of Preferably about 1 cm to about 12 cm, and more preferably about 2 to about 8 cm.

In a preferred embodiment of the invention, the compression lines are not located only along the longitudinal edges but also they complementarily extend toward the regions that do not receive the menstrual discharge directly, but rather they have a direction tending toward each other until they meet and go on in both directions. This is justified by the fact that, in this embodiment, the more rapid and homogeneous distribution of the liquid collected in the absorbing element is optimized.

However, this does not exclude embodiments in which the compression lines do not meet or are radially subdivided or any other embodiment that can distribute the collected liquid without being considerably detrimental to the ability to form a protuberance between the compression lines when subjected to the pressure of the user's thighs.

The present invention will be illustrated in connection with the disposable sanitary pad described and claimed in Brazilian Patent Application PI 8601226 is illustrated. It is understood that this example is given merely by way of illustration and is not intended to limit the scope of the appended claims.

BRIEF DESCRIPTION OF THE DRAWINGS

In the appended drawings:

FIG. 1b is a schematic cross-section taken along the line I—I of FIG. 1a;

FIG. 2b is a schematic cross-section taken along line II—II of FIG. 2a;

DESCRIPTION OF THE PREFERRED EMBODIMENT

Figure 1A:
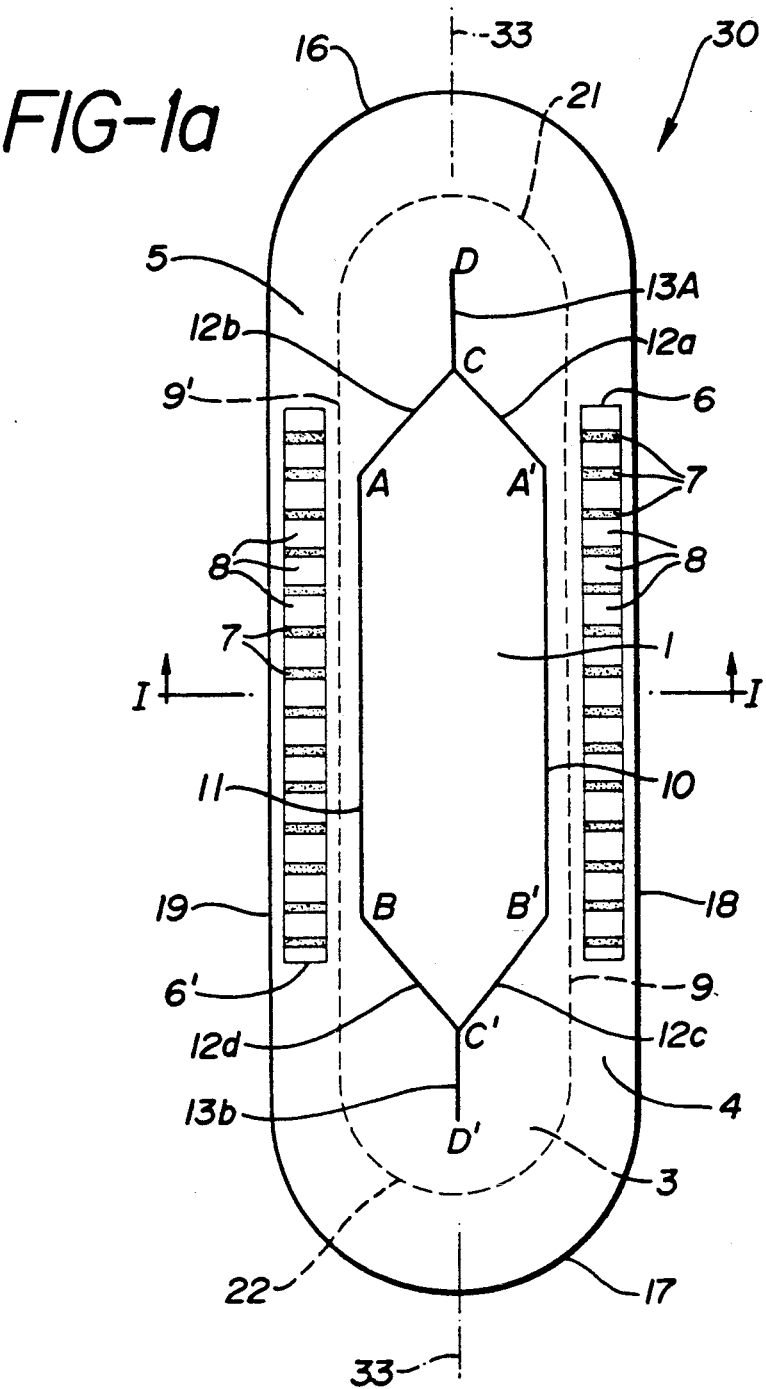
FIG. 1a is a top plan view of the Product before thermocontraction of the elastic means employed.

Referring now to the accompanying drawings, there is shown an external sanitary pad 30 in accordance with the teachings of the present invention. Pad 30, which is elongated in configuration and has rounded upper and lower end edges 16 and 17, respectively, comprises a fluid-permeable facing sheet 1, an absorbing element or absorbent core 3, and a fluid impermeable backing sheet 2. Pad 30 further comprises a pair of elastic elements 6,6' located adjacent longitudinal side edges 18,19, respectively, of the pad. Pad 30 includes compression lines 10, 11, 12a, 12b, 12c, 12d, 13a and 13b which will be described in greater detail hereinafter. As can be seen, for example, in FIG. 1b of the drawings, facing sheet 1 and backing sheet 2 are coextensive in width. Sheets 1 and 3 are also coextensive in length. The absorbing element 3 has a length which is less than the length of the facing and backing sheets and a width which is less than the width of the facing and backing sheets. Absorbing element 3 has a pair of longitudinal side edges 9,9', a rounded top edge 21, and a rounded bottom edge 22 which, taken together, define the perimeter of the absorbing element. The absorbing element is located between facing sheet 1 and backing sheet 2 in the manner best seen in FIG. 1b of the drawings. Facing sheet 1 and backing sheet 2 are secured to each other, e.g. by heat-sealing, in their marginal portions, that is, those portions lying between the perimeter of the absorbing element 3 and the perimeter of pad 30 which is defined by the aforementioned top edge 16, bottom edge 17, and two longitudinal side edges 18,19. Longitudinal side flaps 4,5 are provided in sanitary pad 30 as a result of the securing together of sheets 1 and 2 in the manner just mentioned.

Figure 1B:
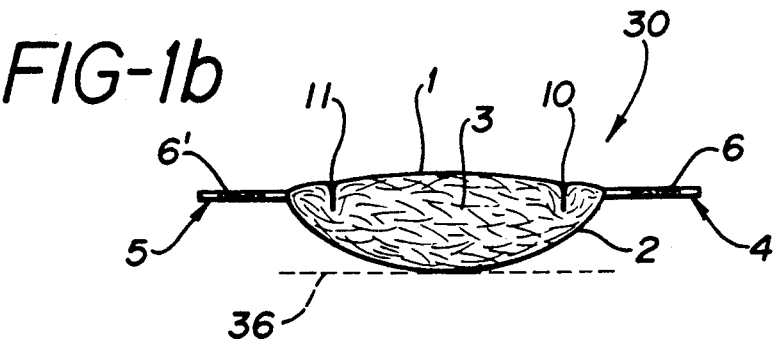
Figure 2A:
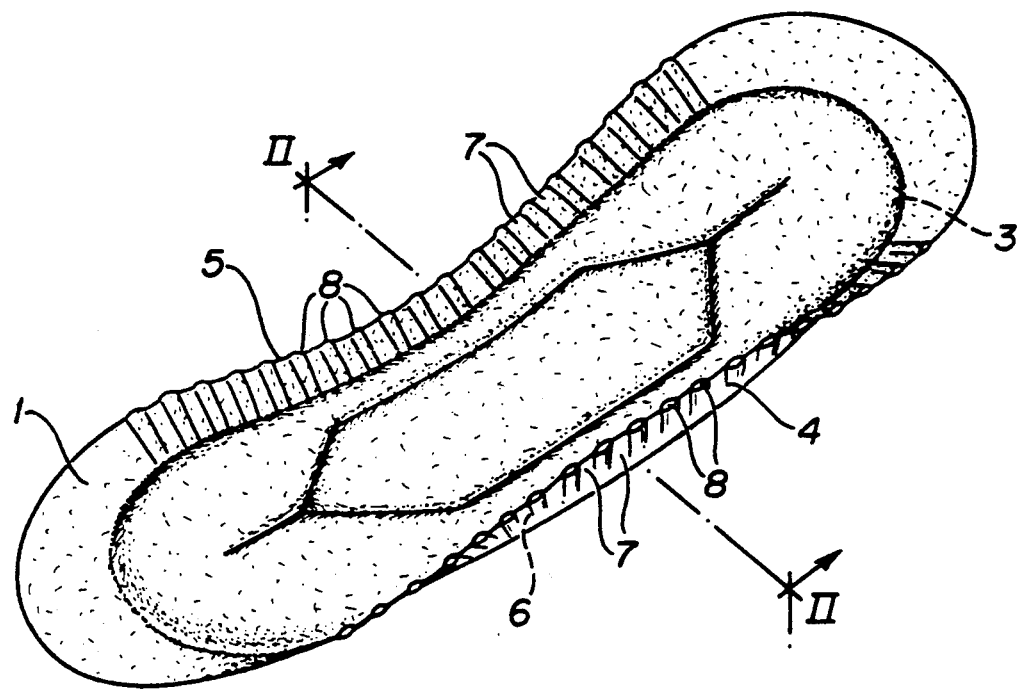
FIG. 2a is a Perspective view of the pad of FIG. 1 after thermocontraction of the elastic means employed.
Figure 2B:
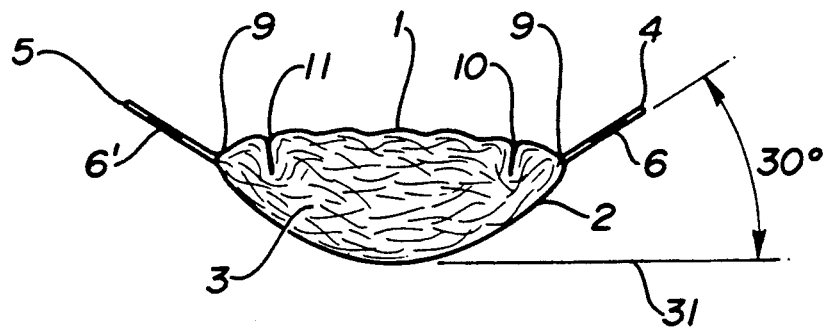

Elastic elements 6,6' are located between facing sheet 1 and backing sheet 2 in longitudinal flaps 4,5, respectively, of pad 30. These elastic elements are in an extended but elastically contractable state when pad 30 is in the flat configuration shown in FIG. 1a. When the elastic elements are permitted to retract from their extended state, the sanitary pad assumes the "boat-like" configuration shown in FIG. 2a. The elastic elements may comprise one or more rubber monofilaments which are secured, e.g. by the use of a hot melt adhesive, between the facing and backing sheets in the manner seen in FIG. 1b. Preferably, however, a strip of thermoplastic film which contracts and becomes elastic upon treatment with heat is used for the elastic elements. Several heat shrinkable thermoplastic films which have elastic properties after being heat shrunk are known in the art. We prefer to use strips of a heat shrinkable copolymer of ethylene and vinyl acetate having a basis weight of about 35g per square centimeter, a length of about 13 cm, a width of about 1 cm and a thickness of about 30 microns. Preferably, the elastic elements have a length which is about 60% of that of the pad 30 and are centered from end to end of the pad. The aforementioned strips of heat shrinkable copolymer are secured in their relaxed state between the facing and backing sheets by the use of heat sealing equipment which provides a series of spaced, transversely oriented lines of securement 7 as shown in FIG. 1a. Lines of securement 7 are separated one from the other by regions 8 in which there is no sealing. When the heat shrinkable elastic elements 6 are secured between the facing and backing sheets by the use of heat-sealing procedures as just described, the heat which is applied will also serve to contract the elements 6,6' and thereby provide them with their elastic properties. If the heat shrinkable elastic elements 6,6' are secured by the use of e.g. an adhesive, it is necessary to thereafter treat those elements with heat, e.g. by the use of hot air, in order for them to contract and obtain their elastic characteristics. When the elastic elements 6,6' are in their retracted state, the sanitary pad 30 assumes the anatomical, shell-like conformation shown in FIGS. 2a and 2b. Side flaps 4,5 and portions of the sanitary pad adjacent thereto are raised upwardly so that, as seen in FIG. 2b, the flaps form an angle of about 30° to the horizontal plane 36 of Pad 30 in its flat configuration illustrated in FIG. 1b.

Preferably, although not necessarily, the fluid-permeable facing sheet 1 is a nonwoven fabric comprising heat-sealable polyester fibers and having a basis weight of 22 g/m with 144 perforations Per square inch. Fluid-impermeable layer 2 preferably comprises a film of polyethylene having a basis weight of 19 g/cm$^2$ and a thickness of about 0.020 mm. When facing sheet 1 comprises heat-sealable polyester fibers and backing sheet 2 comprises polyethylene, the facing and backing sheets may be sealed together in their marginal portions by heat sealing techniques. In the preferred embodiment, absorbing element 3 comprises a layer of 100% wood pulp fluff having a weight of about 7 grams. In a typical sanitary pad, absorbing element 3 is about 20 cm in length and about 6 cm in width. Absorbing element 3 is sandwiched between liquid-permeable facing sheet 1 and liquid-impermeable backing sheet 3 in known fashion.

In one embodiment of the invention, sanitary pad 30 comprises a first pair of compression lines 10,11 running parallel to the longitudinal side edges 9,9' of absorbing element 3. For a sanitary Pad 30 having a length of 22 cm, compression lines 10,11 are conveniently about 6 cm in length (between points A and B and between points A' and B' in FIG. 1a) and are spaced slightly inwardly (about 0.8 cm) from the longitudinal side edges 9,9' of absorbing element 3. The compression lines 10,11 are substantially centrally located between the top and bottom edges of the pad.

In a second and more preferred embodiment, sanitary pad 30 further comprises four additional compression lines. As seen in FIG. 1a, a pair of compression lines extends at an angle from the ends of each compression line 10,11 toward points (C and C' in FIG. 1a) which lie on the longitudinal centerline 33 of sanitary pad 30. Thus, at the upper end of pad 30, a third compression line 12a extends from the upper end A' of first compression line 10 to a first point C located on centerline 33 between said end A and the upper edge 16 of the pad. Similarly, a fourth compression line 12b extends from the upper end A of second compression line 11 to first point C. A second pair of angularly disposed compression lines 12c,12d is provided near the bottom portion of the sanitary pad. Fifth compression line 12c extends from the lower end B' of first compression line 10 to a second point C' located on centerline 33 between said end B' and the lower edge 17 of pad 30. A sixth compression line 12d extends from the lower end B of second compression line 11 to second point C' located on centerline 33.

It will be observed that when compression lines 10, 11, 12a, 12b, 12c, and 12d are disposed in the manner just described, they form the elongated hexagonal configuration best seen in FIG. 1a.

Still referring to FIG. 1a, first compression line 10 and second compression line 11 run parallel to each other and to longitudinal side edges 9,9' of absorbing element 3. In a typical sanitary pad 30 having a length of about 22 cm and a width of about 8 cm and comprising an absorbing element 3 having a length of about 20 cm and a width of about 6 cm, compression lines 10 and 11 have a length of about 6 cm and a width of about 0.15cm. Typically, compression lines 10 and 11 would be separated by a distance of about 4 cm.

In another embodiment of the invention, sanitary pad has a further Pair of compression lines extending along longitudinal centerline 33. Thus, as seen in FIG. 1a, a seventh compression line 13a extends from point C to point D on longitudinal centerline 33 in the direction of the upper end of the sanitary Pad. Similarly, an eighth compression line 13b extends from point C' to point D' on a longitudinal centerline 33 in the direction of the lower end of the sanitary pad. When pad 30 and compression lines 10, 11, 12a, 12b, 12c, and 12d have the typical lengths mentioned hereinabove, compression lines 13a and 13b typically have a length of 1.5 cm. It will be recognized by those skilled in the art that the various dimensions mentioned herein for pad 30, absorbing element 3 and the several compression lines are typical dimensions only and these dimensions may be varied without departing from the spirit and scope of the invention.

A steel plate having ridges corresponding to the desired pattern of compression lines may be employed to form the aforementioned compression lines. By way of illustration, the absorbing element may be placed on a fixed surface and thereafter covered with said steel plate so that the ridges thereof are in contact with the upper surface of the absorbing element. The steel plate is then pressed against the absorbing element, using a Norgren hydraulic press at a Pressure of 9 psi, to form the compression lines.

Figure 3:
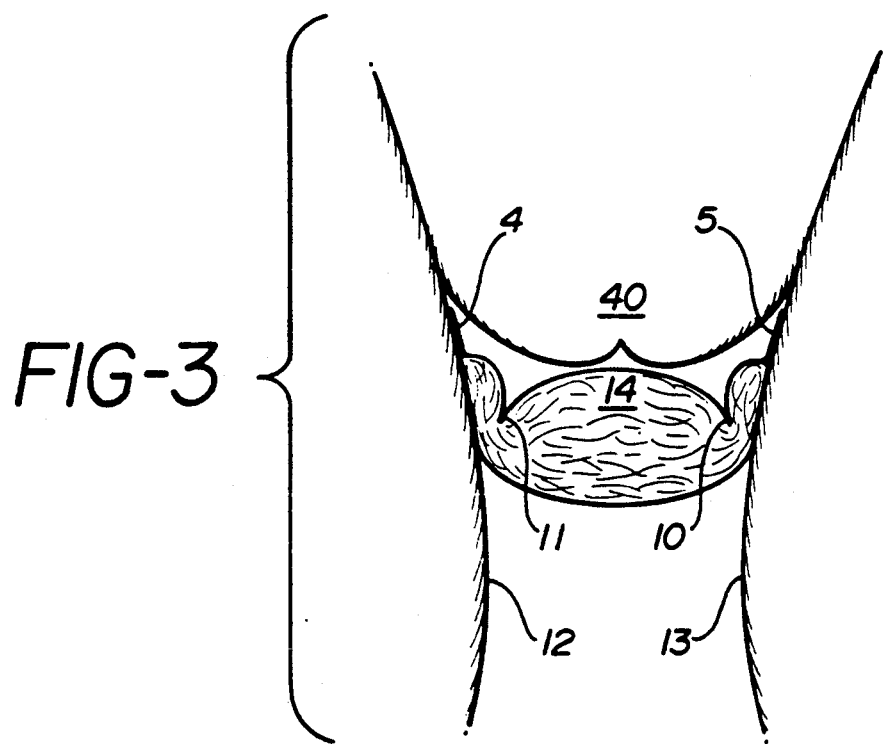
FIG. 3 is a schematic cross-section of the configuration assumed by the sanitary pad of FIG. 1a when in use.

FIG. 3 shows the pad of FIG. 2 in use, placed into contact with the perineal area 40 of the user. Under Pressure of the user's thighs 12 and 13, the protuberance 14 is formed between the compression lines 10,11. The flaps 4 and 5 lie against the user's thighs and are also useful for restricting leakage from the sides.

Figure 4:
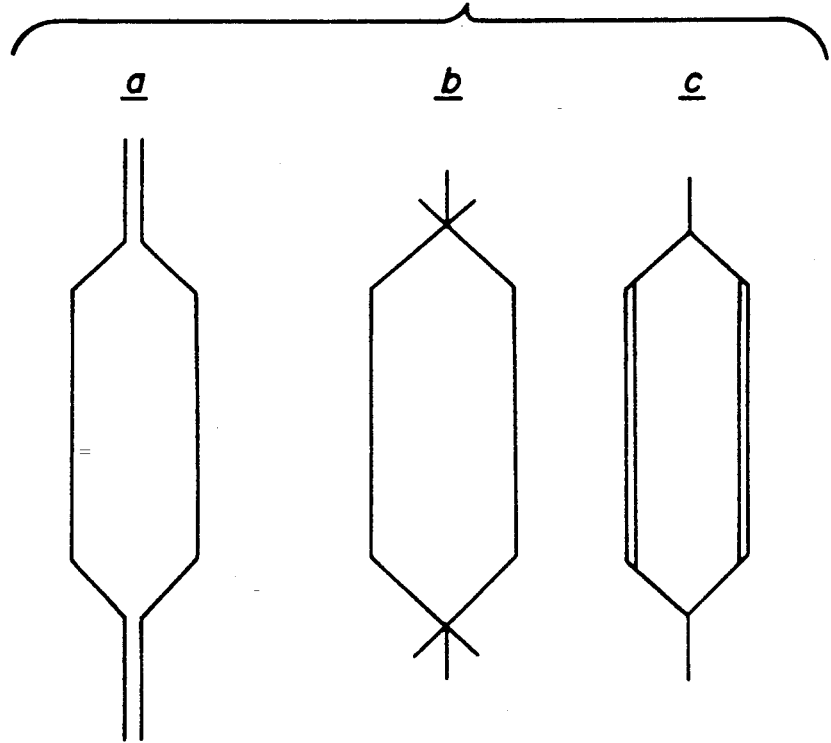
FIG. 4 shows a schematic representation of other arrangements of compression lines which may be utilized in the practice of the present invention.

FIG. 4 shows three examples of the conformation of compression lines used in the invention. Under a the compression lines do not meet; under b the compression lines meet and diverge radially toward the farthest areas of the Pad; under c two compression lines are employed along each longitudinal edge.

A test has been carried out with the sanitary pad of the invention, as illustrated in FIG. 2, with a group of 17 women.

Each woman received 7 pads according to the invention, that is, with compression lines (called herein Group A pads) and another 7 pads similar to the previous ones but without the compression lines (called herein Group B pads).

Each woman wore the pads during the menstruation period, alternating Group A and Group B pads. The average time of use of each pad was 4 hours.

After use, each pad was checked concerning the formation of the central protuberance, and the occurrence of leakage through the sides.

The results were:

40% more products from Group A than from Group B pads showed the formation of the central protuberance, putting in evidence the fact that the use of compression lines as disclosed by the invention lead to their formation.

5% less products from Group A than from Group B pads showed signs of leakage at the sides, showing that the protuberance near the discharge point as disclosed by the invention helps to prevent leakage.

I claim:

1. A disposable sanitary pad comprising:
   (a) an absorbing element comprising longitudinal and transverse centerlines, first and second longitudinal edges, first and second transverse ends, and a body facing side; and
   (b) first and second compression lines formed in said absorbing element, each of said lines comprising:
      (i) a central segment extending substantially longitudinally so that a central portion of said body facing side is disposed between said central segments, said lines formed by compression on said body facing side so that pressure against said longitudinal edges by a user's thighs causes said body facing side of said central portion to assume a convex shape so as to protrude toward a user's body; and
      (ii) each of said first and second compression lines having a first end segment connected to said central segment, said first end segments extending both toward each other and toward said first transverse end so as to form an acute angle with said longitudinal centerline, whereby at least a first portion of fluid deposited proximate said transverse centerline is wicked along said compression lines toward a portion of said absorbing element disposed along said longitudinal centerline and proximate said first transverse end;

wherein said first end segment of said first compression line is connected to said first end segment of said second compression line.

2. A pad according to claim 1, characterized in that said compression lines are about 1 to about 12 cm long.

3. A pad according to claim 1, characterized in that the compression lines are pressed onto the structure that constitutes said pad.

4. A pad according to claim 1 wherein said compression lines are about 1.5 to about 5 mm wide.

5. A pad according to claim 1 wherein said central segments of said compression lines are parallel to said longitudinal edges.

6. A pad according to claim 1 wherein said central segments of said compression lines are parallel to each other.

7. A pad according to claim 1 wherein said compression lines are pressed into said absorbing element.

8. A pad according to claim 1 wherein said absorbing element has a permeable layer covering said body facing side, and wherein said compression lines are pressed into said absorbing element and said permeable layer.

9. A pad according to claim 1 wherein each of said first end segments extends toward the other until they meet and then extend along the longitudinal direction.

10. A pad according to claim 1 wherein the distance from each of said central segments of said compression lines to the nearest longitudinal edge is about 5 to about 30 percent of the transverse width of said absorbing element.

11. A pad according to claim 1 wherein the distance from each of said central segments of said compression lines to the nearest longitudinal edge is about 5 to about 20 percent of the transverse width of said absorbing element.

12. A pad according to claim 1, wherein said central segment of said first compression line is disposed closer to said first longitudinal edge than to said second longitudinal edge, and wherein said central segment of said second compression line is disposed closer to said second longitudinal edge than to said first longitudinal edge.

13. A pad according to claim 1, wherein said first and second compression lines each have second end segments, said second end segments extending both toward each other and toward said second transverse end so as to form an acute angle with said longitudinal centerline, whereby at least a second portion of said fluid deposited proximate said transverse centerline is wicked along said compression lines toward a portion of said absorbing element disposed along said longitudinal centerline and proximate said second transverse end.

14. A pad according to claim 13, further comprising third and fourth compression lines formed in said absorbing element by compression on said body facing side, said third compression line connected to said first end segments of said first and second compression lines and extending substantially longitudinally toward said first transverse end, said fourth compression line connected to said second end segments of said first and second compression lines and extending substantially longitudinally toward said second transverse end, whereby at least a portion of each of said first and second portions of said fluid deposited proximate said transverse centerline and wicked along said first and second compression lines is also wicked along said third and fourth compression lines further toward said first and second transverse ends, respectively.

15. A pad according to claim 13, wherein said second end segment of said first compression line is connected to said second end segment of said second compression line so that said first and second compression lines combine to form an approximately elongated hexagonal shape.

16. A pad according to claim 1, further comprising a third compression line formed in said absorbing element by compression on said body facing side, said third compression line connected to said first end segments of said first and second compression lines and extending substantially longitudinally toward said first transverse end, whereby at least a portion of said portion of said fluid deposited proximate said transverse centerline and wicked along said first and second compression lines is also wicked along said third compression line further toward said first transverse end.

17. A pad according to claim 1, further comprising a third compression line formed in said absorbing element by compression on said body facing side, said third compression line connected to said first end segment of said first compression line and extending substantially longitudinally toward said first transverse end, whereby at least a portion of said portion of fluid deposited proximate said transverse centerline and wicked along said first compression line is further wicked along said third compression line further toward said first transverse end.

18. A pad according to claim 1, wherein said compression lines each have a width of less than approximately 5 mm.

19. A pad according to claim 1, wherein said absorbing element, when uncompressed, has a first density and said compression lines each have a second density greater than the first density, whereby said compression lines are capable of wicking fluid there-along.

* * * * *